United States Patent
Onomichi et al.

(10) Patent No.: US 7,174,266 B2
(45) Date of Patent: Feb. 6, 2007

(54) ANALYZER AND COMPUTER PROGRAM PRODUCT

(75) Inventors: Hiromi Onomichi, Kobe (JP); Masakazu Fukuda, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 11/213,699

(22) Filed: Aug. 30, 2005

(65) Prior Publication Data

US 2006/0064270 A1    Mar. 23, 2006

(30) Foreign Application Priority Data

Sep. 17, 2004    (JP) .............................. 2004-271334

(51) Int. Cl.
*G06F 15/00* (2006.01)
(52) U.S. Cl. ...................... 702/127; 702/189
(58) Field of Classification Search ................... 73/863; 702/85, 127, 189
See application file for complete search history.

(56) References Cited

U.S. PATENT DOCUMENTS

| | | | |
|---|---|---|---|
| 5,038,109 A | 8/1991 | Goble et al. | |
| 5,851,487 A * | 12/1998 | Katayama et al. | 422/68.1 |
| 2005/0261605 A1 * | 11/2005 | Shemer et al. | 600/573 |

* cited by examiner

*Primary Examiner*—John Barlow
*Assistant Examiner*—Douglas N Washburn
(74) *Attorney, Agent, or Firm*—Sughrue Mion, PLLC

(57) ABSTRACT

An analyzer that comprises a sample measuring mechanism for measuring a sample and generating a measurement value, a memory for storing a plurality of standard values for evaluation of the measurement value, the plurality of standard values including a fixed standard value and a variable standard value, a controlller for evaluating the measurement value based on the standard values; and an output device for outputting result of the evaluation of the measurement value by the evaluation means is disclosed. A computer program product is also disclosed.

20 Claims, 15 Drawing Sheets

Fig.12

Standard values table 71

|  | Lower limit values | Upper limit values |
|---|---|---|
| RANK1 | 0 | 5 |
| RANK2 | 5.1 | 16 |
| RANK3 | 16.1 | 27 |
| RANK4 | 27.1 | 38 |
| RANK5 | 38.1 |  |

ANALYZER AND COMPUTER PROGRAM PRODUCT

FIELD OF THE INVENTION

The present invention relates to an analyzer and computer program product, and specifically relates to an analyzer and computer program product providing a function for evaluating measurement values.

BACKGROUND

Conventional devices are known which provide settable standard values (upper limit value and lower limit value) for evaluation (ranking) of measurement values (for example, refer to U.S. Pat. No. 5,851,487).

The device disclosed in U.S. Pat. No. 5,851,487 is allows changing of the standard values. Therefore, a user of this analyzer can change the standard values in accordance with the purpose for which the analyzer is used. For example, it is possible to have separate standard values for analyzing specimens from hospitalized patients, and standard values for analyzing specimens from persons undergoing routine health examinations, and, therefore, it is possible to accurately rank the measurement values.

However, the standard values used in ranking measurement values include standard values that may be optionally changed by the user of the analyzer, and standard values that cannot be optionally changed.

For example, since analyzers often do not operate normally when measurement values fall into a ranking representing a lowest value and a ranking representing a highest value, the standard values for these rankings may not be optionally changed by a user.

Since this point has not been considered in the case of conventional analyzers, however, it is difficult to accurately set standard values.

SUMMARY

The scope of the present invention is defined solely by the appended claims, and is not affected to any degree by the statements within this summary.

An object of the present invention is to provide an analyzer and computer program product that provide easy and accurate setting of standard values for evaluating measurement values.

A first aspect of the present invention is an analyzer comprising: a sample measuring section for measuring a sample and generating a measurement value; a memory for storing a plurality of standard values for evaluation of the measurement value, the plurality of standard values including a fixed standard value and a variable standard value; an evaluation means for evaluating the measurement value based on the standard values; and an output device for outputting result of the evaluation of the measurement value by the evaluation means.

A second aspect of the present invention is a computer program product comprising: a first computer code for measuring a sample and generating a measurement value; a second computer code for storing a plurality of standard values for evaluation of the measurement value, the plurality of standard values including a fixed standard value and a variable standard value; a third computer code for evaluating the measurement value based on the standard values; and a fourth computer code for outputting result of the evaluation of the measurement value.

A third aspect of the present invention is an analyzer comprising: a sample measuring section for measuring a sample and generating a measurement value; a display device; a memory for storing first and second standard values for evaluating the measurement value; a first standard value setting means for displaying a first screen including the first standard value on the display device, and receiving a change of the first standard value; and a second standard value setting means for displaying a second screen including the second standard value on the display device, and receiving a change of the second standard value.

BRIEF DESCRIPTION OF THE DRAWINGS

FIG. 12 is a structural diagram showing the structure of a standard value table 71;

DETAILED DESCRIPTION OF THE PREFERRED EMBODIMENTS

The preferred embodiments of the present invention are described hereinafter with reference to the drawings.

The embodiments below are described in terms of a urine analyzer for analyzing tangible material in urine as an example of the analyzer of the present invention.

Figure 1:
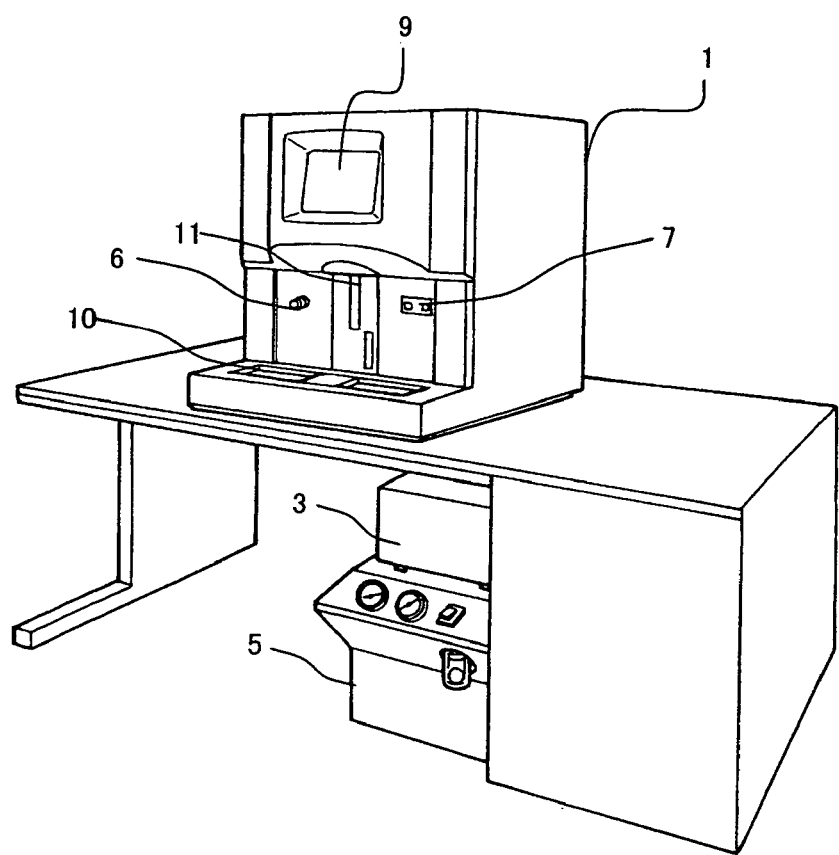
FIG. 1 is a perspective view showing the general structure of a urine analyzer of an embodiment of the present invention.

The urine analyzer of the present embodiment for analyzing tangible materials in urine is provided with an analyzer body 1, laser power supply 3, and vacuum source 5 as shown in FIG. 1.

The analyzer body 1 is provided with a power switch 6, transport unit 10 for automatically conveying specimen containers containing urine as samples to a suction unit 11, suction unit 11 for suctioning urine from the specimen container, start switch 7 for starting the suctioning of urine by the suction unit 11, and a touch panel type liquid crystal display 9 (hereinafter referred to as "display 9") for receiving operation instruction input from a user and displaying urine analysis results and the like.

A vacuum source 5, which supplies positive pressure and negative pressure to the analyzer body 1, is connected to the analyzer body 1 through a tube not shown in the drawing. A laser power supply 3, which supplies power to an argon laser described later, is connected to the analyzer body 1 through a cable not shown in the drawing. Reagent containers not shown in the drawing are connected to the analyzer body 1, and the body 1 suctions reagent from the reagent containers using the negative pressure supplied from the vacuum source 5.

Figure 2:
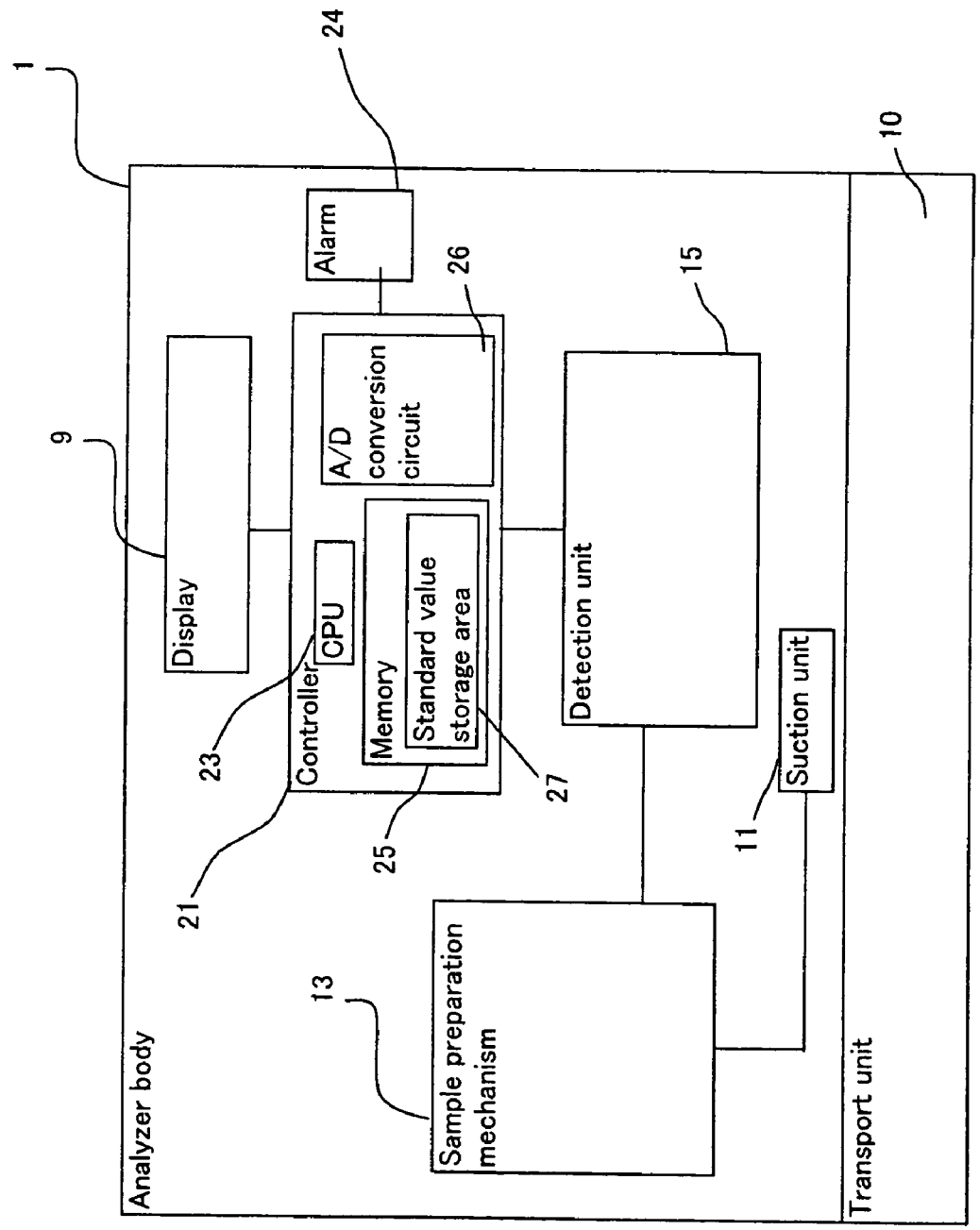
FIG. 2 is a block diagram illustrating the internal structure of the urine analyzer of the embodiment of the present invention.

As shown in FIG. 2, the analyzer body 1 is provided with the transport unit 10, suction unit 11, sample preparation mechanism 13, detection unit 15, controller 21, alarm 24, and display 9.

The sample preparation mechanism 13 prepares a measurement sample by mixing urine suctioned by the suction unit 11, and reagent suctioned from the reagent container, and transports the measurement sample to the detection unit 15.

The detection unit 15 detects detection data such as scattered light data, fluorescence data, and voltage from the measurement sample transported from the sample preparation mechanism 13, and outputs the detection data to the controller 21.

The controller 21 analyzes the detection data output from the detection unit 21, and generates analysis results which are then output to the display 9.

The controller 21 is provided with a CPU 23, A/D conversion circuit 26, and memory 25. The A/D conversion circuit 26 converts the detection data output from the detection unit 15 from analog values to digital values, which are then output to the memory 25.

The memory 25 is provided with ROM and RAM. Programs for operating the analyzer body 1 described later are stored in ROM. Standard value storage area 27 for storing standard values described later is provided in RAM. Detection data output from the detection unit 15 are stored in RAM.

The alarm 24 is a sound generating device for generating a warning sound and an operating sound in accordance with directions from the controller 21.

Figure 3:
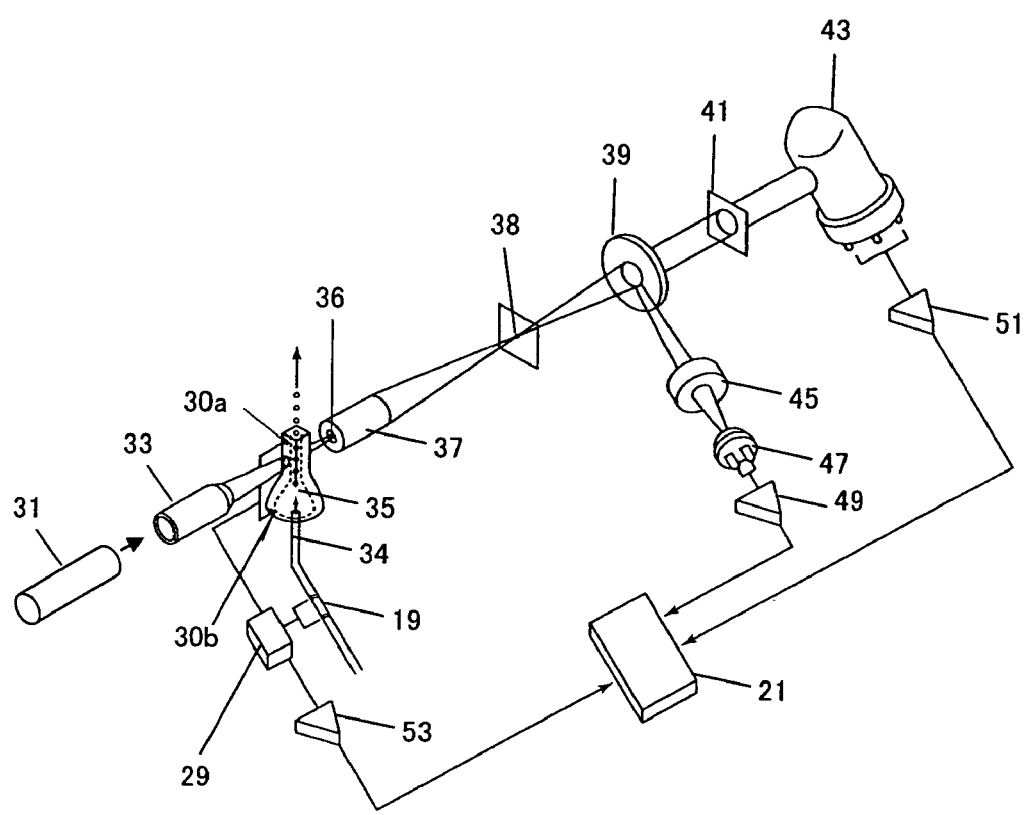
FIG. 3 is a structural diagram showing the structure of the detection unit 15 shown in FIG. 2.

As shown in FIG. 3, the detection unit 15 is provided with a conductivity sensor 19, direct current power supply circuit 29, electrodes 30a and 30b, argon laser 31, illumination lens system 33, sample nozzle 34, flow cell 35, beam stopper 36, collector lens 37, pinhole 38, dichroic mirror 39, filter 41, photomultiplier 43, lens 45, photodiode 47, and amplifiers 49, 51, and 53.

A measurement sample transported from the sample preparation unit 13 flows through the conductivity sensor 19 and sample nozzle 34 to the flow cell 35.

Light emitted from the argon laser 31 is collected by the illumination lens system 33, and irradiates the measurement sample flowing through the flow cell 35. The light which has irradiated the measurement sample is scattered, and collected by the collector lens 37, light that is not required for measurement is eliminated by the pinhole 38, and the remaining light irradiated the dichroic mirror 39. The beam stopper 36 blocks the directly irradiating light from the argon laser 31. The argon laser 31 generates laser light using power supplied form the laser power supply 3. A light-emitting diode (LED) and lasers such as a helium neon laser, red semiconductor laser, or blue semiconductor laser may be alternatively used in place of the argon laser 31.

The light illuminating the dichroic mirror 39 is separated into a scattered light component and a fluorescent light component. The scattered light component is collected by the lens 45, and irradiates the photodiode 47. Only the fluorescent light component of specific wavelength is transmitted by the filter 41, and irradiates the photomultiplier 43.

The photodiode 47 and photomultiplier 43 output electric signals which correspond to the intensity of the irradiating light. The output electric signals are amplified by the amplifiers 49 and 51, and transmitted to the controller 21.

The DC power supply circuit 29 applies a DC current through the electrode 30a and electrode 30b to the measurement sample flowing through the flow cell 35. The DC power supply circuit 29 is provided with a function for detecting the voltage between the electrode 30a and electrode 30b, and the detected voltage is amplified by the amplifier 53 and transmitted to the controller 21.

The conductivity sensor 19 is used for calculating the conductivity of the measurement sample. The conductivity sensor 19 detects the voltage of the measurement sample flowing through. The voltage detected by the conductivity sensor 19 is transmitted through the DC power supply circuit 29 to the amplifier 53, the voltage is amplified by the amplifier 53 and transmitted to the controller 21. The controller 21 calculates (generates) a conductivity from the received voltage.

Figure 4:
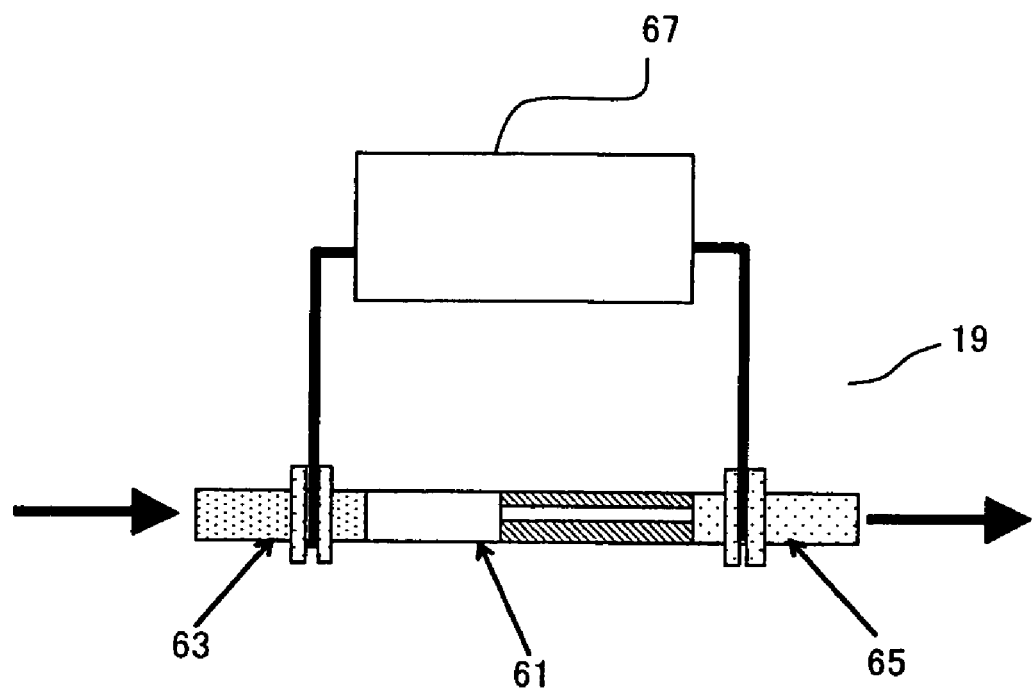
FIG. 4 is a structural diagram showing the structure of the conductivity sensor 19 shown in FIG. 3.

As shown in FIG. 4, the conductivity sensor 19 is provided with a tube 61, electrode 63, electrode 65, and detection circuit 67.

The tube 61 is formed of ceramic material 1 cm in length and has an internal diameter of 1 mm. In FIG. 4, a part of the tube 61 is shown in cross section. The electrodes 63 and 65 are hollow electrodes formed of stainless steel and have an internal diameter of 1 mm, and are connected to the ends of the tube 61. The measurement sample flows within the interior of the electrode 63, tube 61, and electrode 65, through sample nozzle 34 to the flow cell 35.

The detection circuit 67 is connected to the electrodes 63 and 65. The detection circuit 67 has the functions of supplying a current which flows through the electrode 63, measurement sample inside the tube 61, and electrode 65, and detecting and outputting the voltage between the electrodes 63 and 65 obtained while the current flows.

The operation of the urine analyzer of the present embodiment is described below with reference to FIGS. 1~15.

Figure 5:
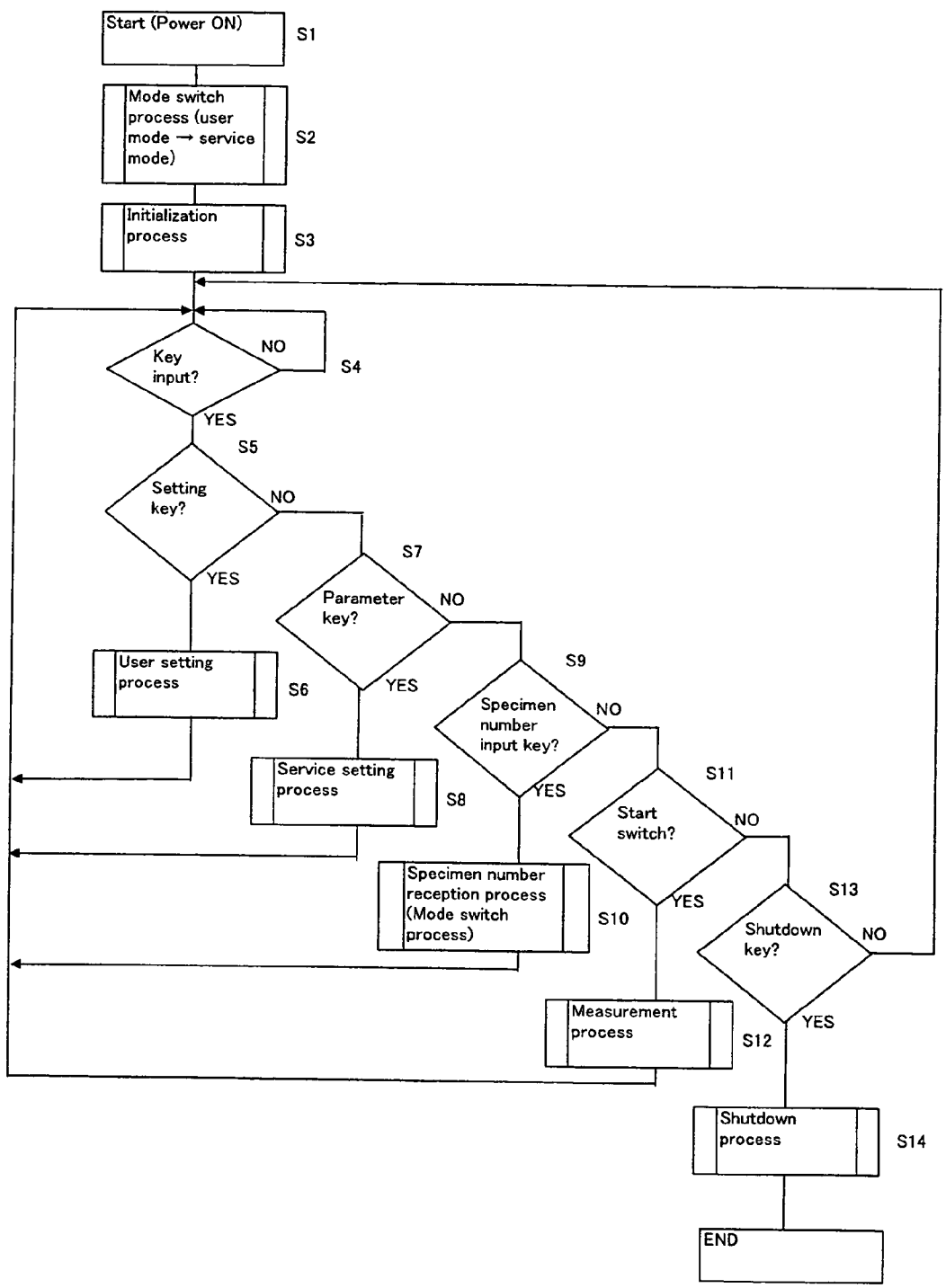
FIG. 5 is a flow chart showing a summary of the processes executed by the controller 21.

A summary of the processes executed by the controller 21 is described below using FIG. 5.

When a user turned ON the power supply of the analyzer body 1 by operating the power switch 6 (step S1), the controller 21 executes a mode switching process (step S2). The mode switching process sets the analyzer body 1 to either the user mode or service mode.

Then, the controller 21 executes an initialization process (step S3). The initialization process includes a process for initializing software (however, the service flag, which is described later, is not changed), and a process for returning the mechanisms such as the suction unit 11 and sample preparation unit 13 and the like to their starting positions. When the initialization process ends, a measurement screen for starting a measurement is displayed on the display 9. The measurement screen includes a parameter key if the analyzer body 1 has been set to the service mode, and does not include the parameter key if the analyzer body 1 has been set to the user mode. That is, the parameter key is displayed on the display 9 when the analyzer body 1 has been set to the service mode, and is not displayed on the display 9 when the analyzer body 1 has been set to the user mode.

Next, the controller 21 determines whether or not there has been input from any key displayed on the measurement screen of the display 9, or the start switch 7 (hereinafter referred to as "key" (step S4).

When there has been key input in step S4, the controller 21 determines whether or not the input key is a setting key (step S5). The setting key is displayed on the display 9 both when the analyzer body 1 is set to the user mode and when the analyzer body 1 is set to the service mode, and is used to display the standard value change screen for the user as described later. When it is determined that the input key is the setting key, the controller 21 executes the user setting process (step S6). The user setting process includes a process for setting predetermined standard values (second standard values) among the standard values for evaluating conductivity of measurement sample in the user mode and the service mode.

When it is determined that the input key is not the setting key in step S5, the controller 21 determines whether or not the input key is the parameter key (step S7). The parameter key is displayed on the display 9 when the analyzer body 1 has been set to the service mode, and is used to display a standard value change screen for service personnel described later. When the input key is determined to be the parameter key, the controller 21 executes the service setting process (step S8). The service setting process includes a process for setting predetermined standard values (first standard values) among the standard values for evaluating the conductivity of the measurement sample.

When it is determined that the input key is not the parameter key in step S7, the controller 21 determines whether or not the input key is the specimen number input key (step S9). When it is determined that the input key is the specimen number input key, the controller 21 executes the specimen number receiving process (step S10). The specimen number receiving process includes a process for receiving the specimen number for specifying the urine (specimen) to be measured. This process includes a switching process for switching from the service mode to the user mode.

When it is determined that the input key is not the specimen number input key in step S9, the controller 21 determines whether or not the input key is the start switch 7 (step S11). When it is determined that the input key is the start switch 7, the controller 21 executes the measurement process (step S12). The measurement process includes a process for measuring the urine, a process for acquiring the measurement values including the numbers of red blood cells (RBC), white blood cells (WBC), epidermal cells (EC), columnar cells (CAST), bacteria (BACT), and conductivity (COND) and the like, and a process for evaluating the measurement values using the standard values.

When it is determined in step S11 that the input key is not the start switch 7, the controller 21 determines whether or not the input key is the shutdown key (step S13). When it is determined that the input key is the shutdown key, the controller 21 executes the shutdown process (step S14). The shutdown process includes a process for washing the suction unit 11 and sample preparation unit 13 and the like, and a process for ending specific programs, and the analyzer body 1 is turned OFF when the shutdown process ends.

Figure 6:
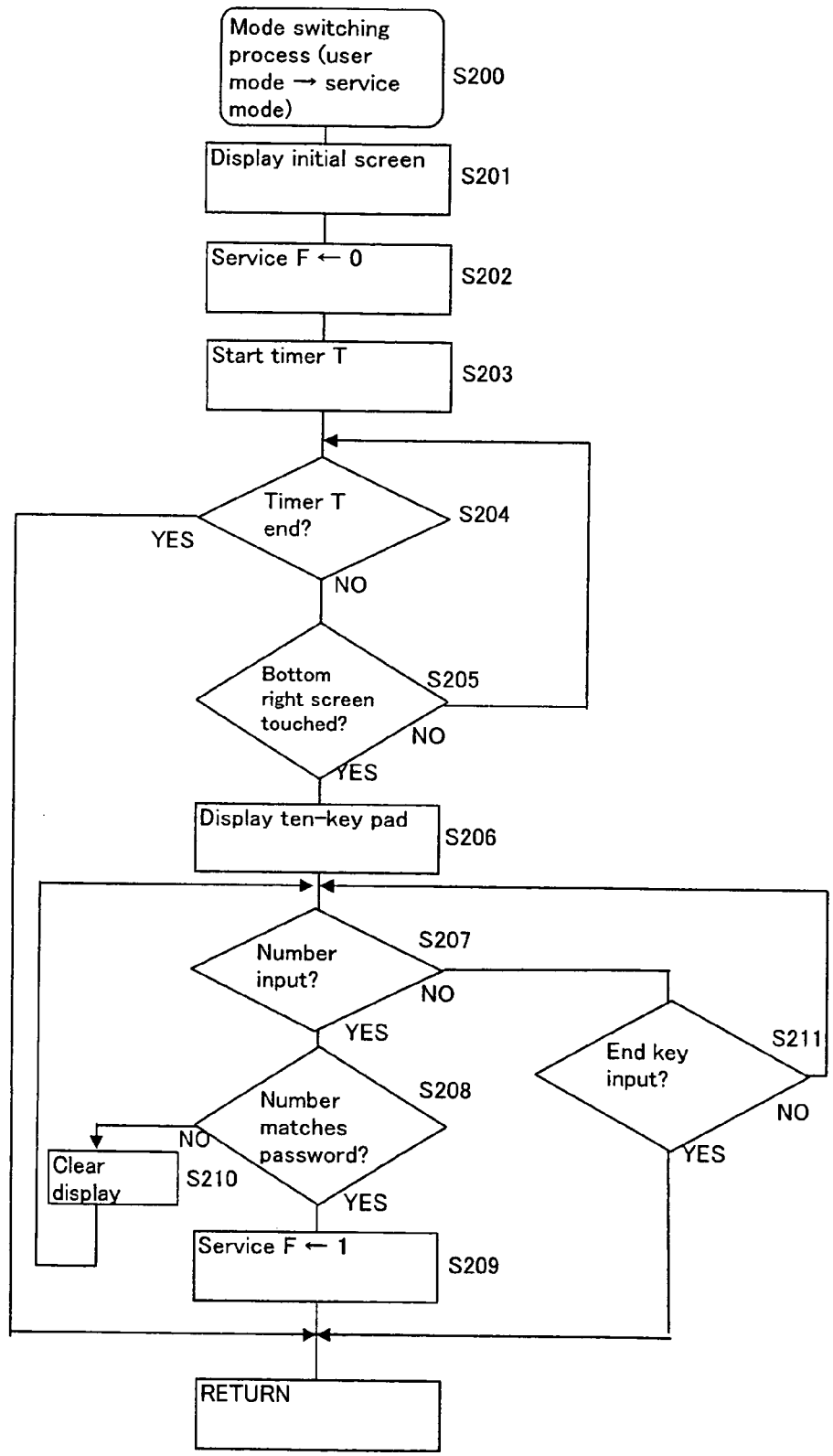
FIG. 6 is a flow chart showing details of the mode switching process (step S2)

Details of the mode switching process of step S2 are described below using FIG. 6.

In step S201, the controller 21 executes a process to display the initiation screen on the display 9.

In step S202, the controller 21 sets the service flag (hereinafter "flag" is abbreviated as "F") to [0].

In step S203, the controller 21 executes a process to start a timer T.

In step S204, the controller 21 executes a process to determine whether or not the timer T has ended. The timer T stops 5 seconds after starting. If the timer T has not ended, then in step S205 the controller 21 executes a process to determine whether or not a predetermined position on the display 9 (bottom right of display 9) has been touched. If the predetermined position has not been touched in step S205, the process to determine whether or not the timer T has ended is again executed (step S204).

When the timer T has ended in step S204, the service flag F remains set at [0] and the routine advances to step S3. In this way the analyzer body 1 operates under the user mode.

There is no display suggesting the user should touch the bottom right of the display 9 (for example a key or button). If only specific persons assigned to maintain the urine analyzer know to touch the predetermined position, then the assigned person can switch the urine analyzer to the service mode, and normal users cannot switch to the service mode. Therefore, the assigned user can change both the first standard values and the second standard values, whereas normal users can change the second standard values but cannot change the first standard values.

Figure 11:
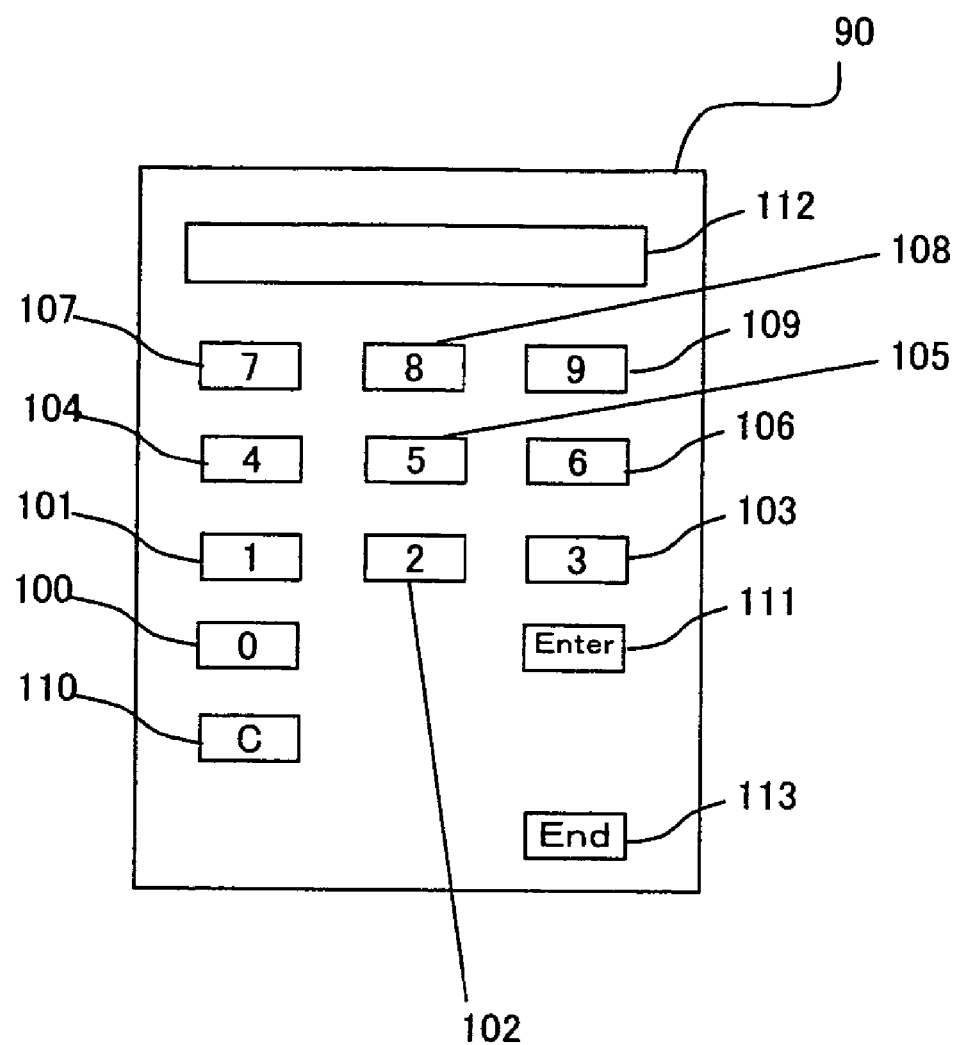
FIG. 11 is a structural diagram illustrating the structure of the ten-key pad 90.

If the predetermined position on the display 9 has been touched in step S205, then the ten-key pad 90 shown in FIG. 11 is displayed on the display 9 (step S206). The ten key pad 90 is provided with ten numeric keys 100~109 for inputting numbers 0~9, cancel key 110 for canceling an input number, input key 111 for accepting an input number, display section 112 for displaying input numbers, and end key 113 for ending password input.

The controller 21 then receives the password (numbers and the like) input by the ten-key pad 90 displayed on the display 9, and executes a process to determine whether or not there is input from the input key 111 (step S207).

When a password (numbers and the like) is input and there is input from the input key 11, the controller 21 executes a process to determine whether or not the input password (numbers and the like) matches a predetermined password (first password) (step S208). The first password includes, for example, four digits and is stored beforehand in the memory 25.

When the input password (numbers and the like) matches the first password, the controller 21 sets the service flag to [1] (step S209). In this way the analyzer body 1 operates under the service mode.

If the input password (numbers and the like) does not match the first password, the controller 21 initializes the display section 112 of the ten-key pad 90 (step S210), and again executes the process of step S207.

If a password (numbers and the like) has not been input in step S207, the controller 21 executes a process to determine whether or not there is input from the end key 113 (step S211). Password input ends when the user touches the end key 113 provided on the ten-key pad 90.

When the end key 113 is touched, the controller 21 ends the mode switching process (step S2), and advances to the initialization process (step S3). In this way the analyzer body 1 operates under the user mode.

When there is no input from the end key 113 in step S211, the controller 21 again executes the process of step S207.

Figure 7:
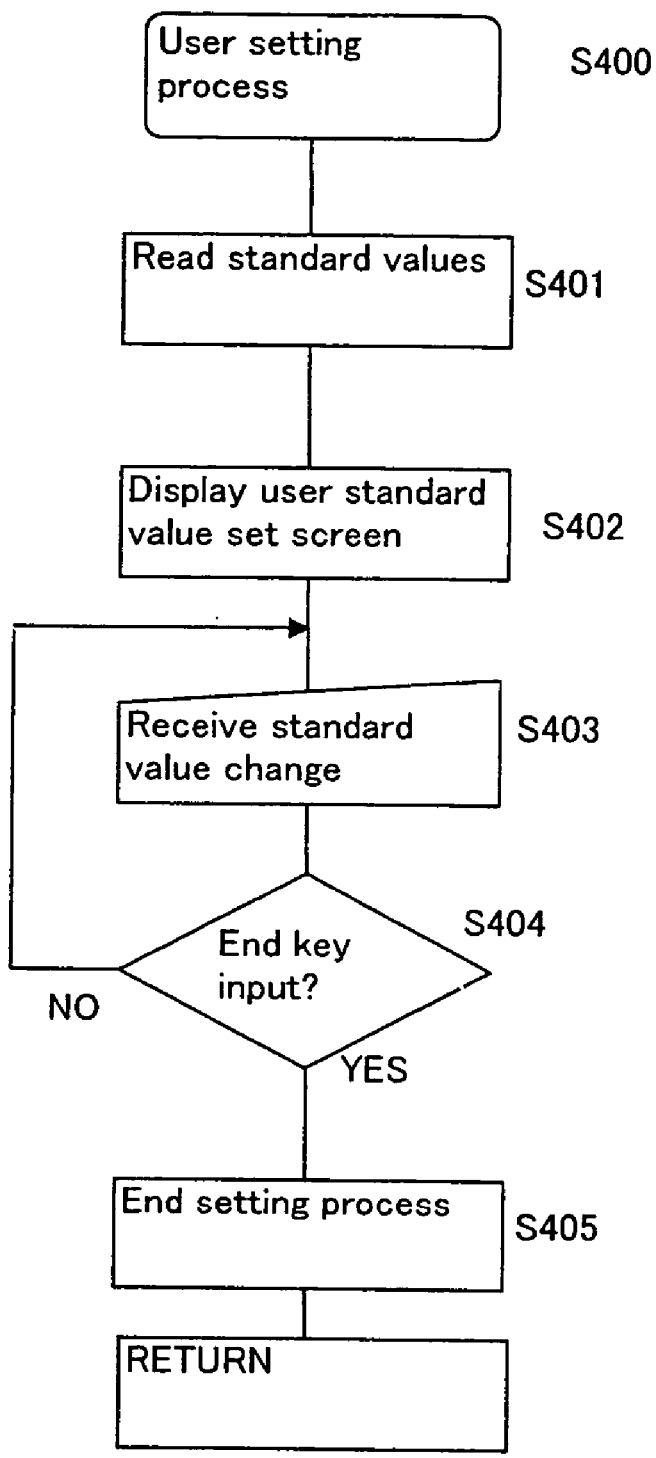
FIG. 7 is a flow chart showing details of the user setting process (step S6)

Details of the user setting process in step S6 are described below using FIG. 7.

In step S401, the controller 21 reads the standard values stored in the standard value storage area 27 of the memory 25.

FIG. 12 shows a standard values table 71 stored in the standard value storage area 27. The standard values included in the standard values table 71 are used to evaluate the conductivity calculated by the controller 21 based on the voltage of the measurement sample detected by the conductivity sensor 19. The standard values table 71 include [0] as a lower limit value (standard value), and [5] as an upper limit value (standard value) of rank 1 which shows the conductivity in the lowest region. Similarly, the standard values table 71 includes 5.1 as a lower limit value (standard value) and 16 as an upper limit value (standard value) of rank 2 in the second lowest region of conductivity, 16.1 as a lower limit value (standard value) and 27 as an upper limit value (standard value) of rank 3 in the third lowest region of conductivity, 27.1 as a lower limit value (standard value) and 38 as an upper limit value of rank 4 in the second highest region of conductivity, and 38.1 as a lower limit value (standard value) of rank 5 in the highest region of conductivity. The lack of an upper limit value for rank 5 indicates that all numeric value equal to or greater than 38.1 are included in rank 5. Furthermore, conductivity can be classified in any rank from rank 1 to rank 5 since the hundredths decimals are rounded off.

When urine is measured there is a very low possibility of classification in rank 1 and rank 5; for example, when conductivity is classified in rank 1, it should be considered that water rather than urine has been measured, or that the analyzer is malfunctioning. However, when conductivity is equivalent to rank 5, it should be considered that the analyzer is malfunctioning. Therefore, it is not desirable for a user of the analyzer to optionally change the range of these ranks.

It is desirable, however, that a user of the urine analyzer should be able to change the ranges rank 2, rank 3, and rank 4 in accordance with the purpose for which the analyzer is used. For example, the standard values when evaluating the conductivity measured in the case of a hospitalized patient, and the standard values when evaluating the conductivity measured in the case of health exam subjects may be separate values.

Then, in step S402, the controller 21 executes a process for displaying the user standard value change screen on the display 9.

Figure 13:
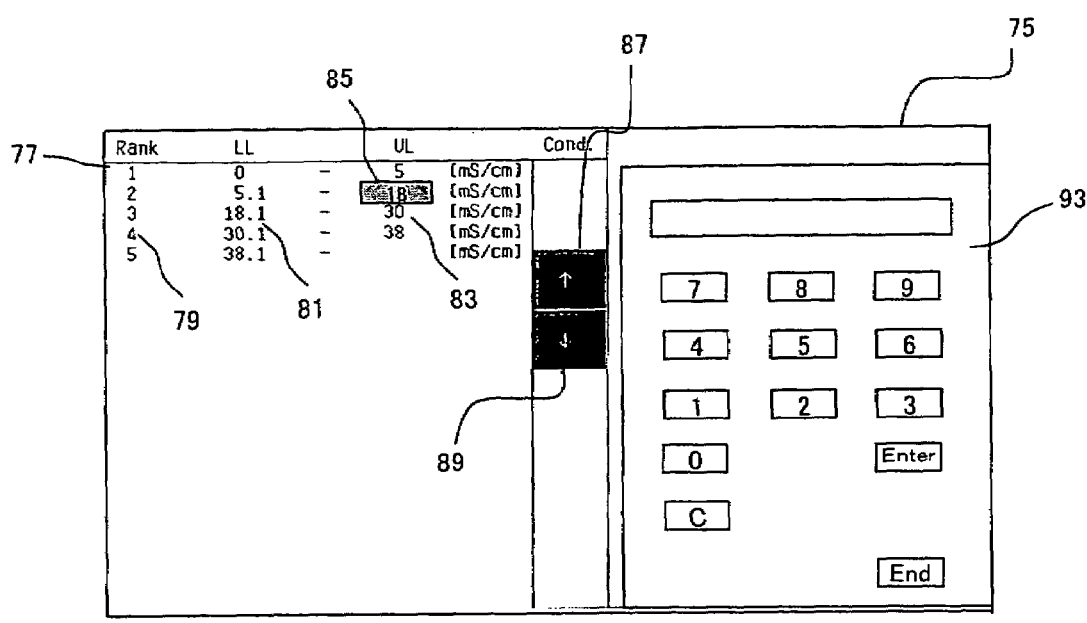
FIG. 13 shows the standard value change screen 75 utilized by the user.

FIG. 13 shows the user standard value change screen 75 displayed on the display 9 in step S402. The user standard value change screen 75 includes a standard value display section 77 for displaying standard values, and a ten-key pad 93. The standard value display section 77 includes a rank display section 79 for displaying numeric values from 1 to 5 indicating rank 1 to rank 5, lower limit display section 81 for displaying the lower limit values from rank 1 to rank 5 displayed adjacent and to the right of the rank display section 79, upper limit display section 83 for displaying the upper limit values from rank 1 to rank 5 displayed adjacent and to the right of the lower limit display section 81, up arrow key 87, and down arrow key 89. Lower limit values read from the standard value storage area 27 in step S401 are displayed in the lower limit display section 81, and upper limit values read from the standard value storage area 27 in step S401 are displayed in the upper limit display section 83.

A cursor 85 is displayed in the upper limit display section 83. The cursor 85 moves up one line each time the user touches the up arrow key 87, and moves down one line each time the user touches the down arrow key 89. The cursor 85 is movable only in the position of the upper limit value of rank 2 (that is, the cursor 85 overlays the position of the numeric value 18) and the position of the upper limit value of rank 3 (that is, the cursor 85 overlays the numeric value 30). When the cursor 85 is at the position of the upper limit value of rank 2 and the user touches the up arrow key 87, the cursor 85 does not move, and the alarm 24 emits a warning sound. When the cursor 85 is at the position of the upper limit value of rank 3 and the user touches the down arrow key 89, the cursor 85 does not move, and the alarm 24 emits a warning sound. In this way the user easily understands that the upper limit values of rank 1 and rank 4 cannot be changed.

The ten-key pad 93 is identical to the previously described ten-key pad 90.

Then, in step S403, the controller 21 executes a process for receiving a change (setting) of the standard values.

With the cursor 85 placed at the position of the upper limit value of rank 2, when the user inputs a numeric value using the ten-key pad 93 and subsequently touches the input key, the upper limit value of rank 2 is changed to the input numeric value. Then, the lower limit value of rank 3 is automatically changed to a numeric value obtained by adding 0.1 to the input numeric value. With the cursor 85 placed at the position of the upper limit value of rank 3, when the user inputs a numeric value using the ten-key pad 93 and subsequently touches the input key of the ten-key pad 93, the upper limit value of rank 3 is changed to the input numeric value. Then, the lower limit value of rank 4 is automatically changed to a numeric value obtained by adding 0.1 to the input value. The upper limit value cannot be changed when a number less than the upper limit value of a next lower rank is input using the ten-key pad 93 and the input key is touched in an attempt to change the upper limit value. The upper limit value cannot be changed when a number greater than the upper limit value of a next higher rank is input using the ten-key pad 93 and the input key is touched in an attempt to change the upper limit value.

In step S404, the controller 21 executes a process to determine whether or not there has been input from the end key of the ten-key pad 93. When the end key of the ten-key pad 93 is touched, the setting of the standard values ends.

When the end key of the ten-key pad 93 is input, then in step S405 the controller 21 executes a process to end setting of the standard values and the routine returns to the process of step S4.

The process for ending the setting of the standard values includes a process for setting the standard values set in step S403 as the upper limit value of rank 2, lower limit value of rank 3, upper limit value of rank 3, and lower limit value of rank 4 of the standard values table 71, and storing these values in the standard value storage area 27 of the memory 25.

The process for ending the setting of the standard values further includes a process for displaying a measurement screen for starting measurement on the display 9.

If there is no input from the end key of the ten-key pad 93 in step S404, the controller 21 again executes the process of step S403.

Figure 8:
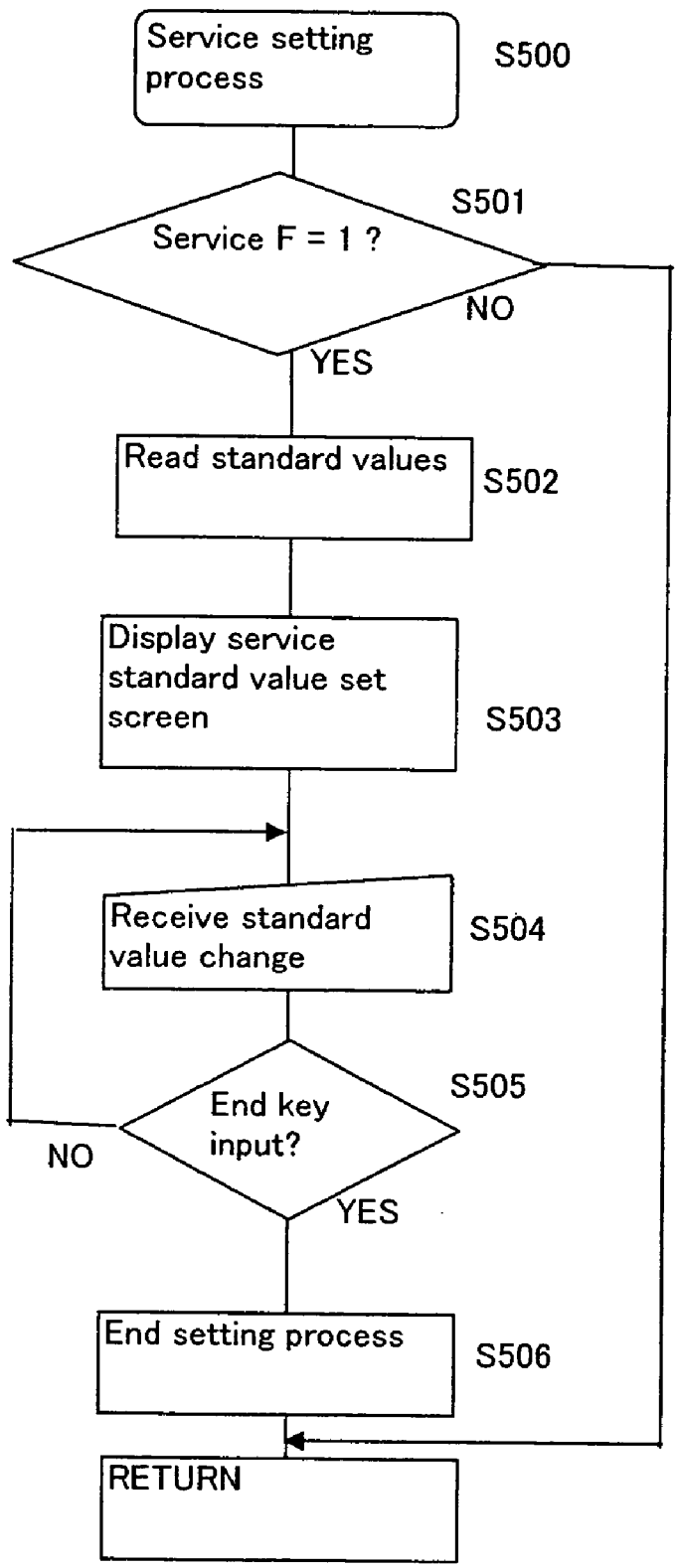
FIG. 8 is a flow chart showing details of the service setting process (step S8)

Details of the service setting process of step S8 are described below using FIG. 8.

In step S501, the controller 21 executes a process to determine whether or not the service F is set at [1].

When it is determined that the service flag F is set at [1], then in step S502 the controller 21 reads the upper limit value of rank 1 and the upper limit value of rank 4 among the standard values stored in the standard value storage area of the memory 25.

Then, in step S503, the controller 21 executes a process for displaying the service standard value change screen on the display 9.

Figure 14:
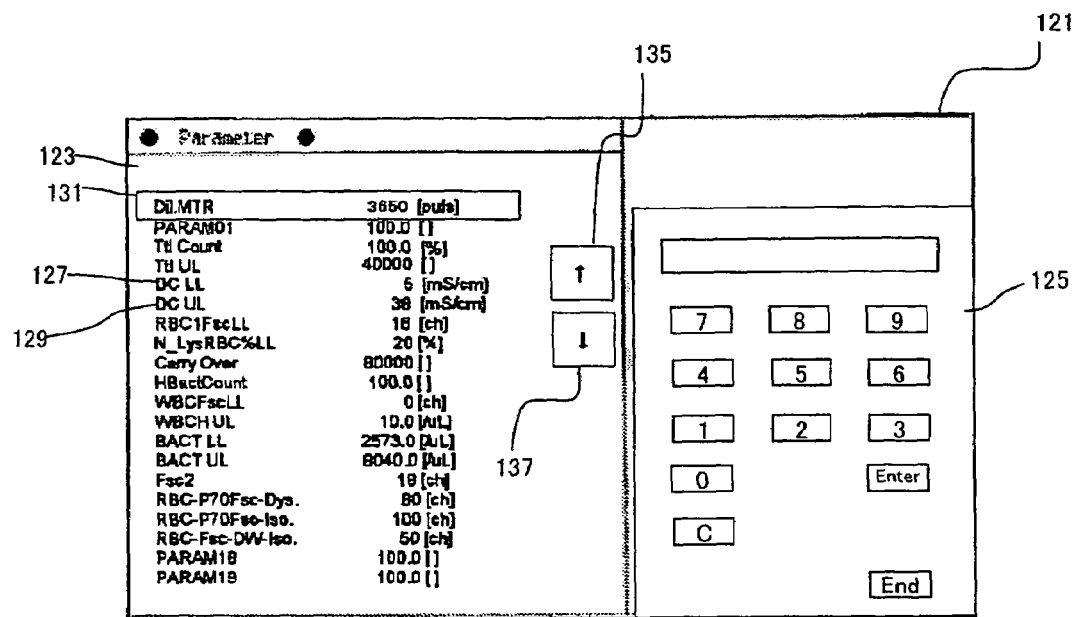
FIG. 14 shows a standard value change screen 121 used by service personnel.

FIG. 14 shows the standard value change screen 121 used by service personnel displayed on the display 9 in step S503. The service standard value change screen 121 includes a parameter display section 123 for displaying various types of parameters, and a ten-key pad 125. The parameter display section 123 includes a standard value display area 127 for displaying [DC LL] indicating the upper limit value of rank 1, standard value display area 129 for displaying [DC UL] indicating the upper limit value of rank 4, cursor 131, up arrow key 135, down arrow key 137 and areas for displaying other parameters. The upper limit value of rank 1 read from the standard value storage area 27 in step S502 is displayed on the standard value display area 127, and the upper limit value of rank 4 read from the standard value storage area 27 in step S502 is displayed on the standard value display area 129.

The cursor 31 moves up one line each time a user touches the up arrow key 135, and moves down one line each time a user touches the down arrow key 137.

The ten-key pad 125 is identical to the previously described ten-key pad 90.

In step S504, the controller 21 executes a process to receive a change in the standard values.

With the cursor 131 aligned on the position of the standard value display area 127, when the user inputs a numeric value using the ten-key pad 125 and touches the input key of the ten-key pad 125, the rank 1 upper limit value (DC LL) is changed to the input numeric value. With the cursor 131 aligned on the position of the standard value display area 129, when the user inputs a numeric value using the ten-key pad 125 and touches the input key of the ten-key pad 125, the rank 4 upper limit value (DC UL) is changed to the input numeric value. With the cursor 131 aligned on the position of the standard value display area 127, when the user inputs a numeric value using the ten-key pad 125 and the numeric value is greater than the upper limit of rank 2, the upper limit value is not changed. With the cursor 131 aligned on the position of the standard value display area 129, when the user inputs a numeric value using the ten-key pad 125 and the numeric value is less than the upper limit value of rank 3, the upper limit value is not changed.

In step S505, the controller 21 executes a process to determine whether or not there has been input from the end key of the ten-key pad 125. When the end key of the ten-key pad 125 is touched, the setting of the standard values ends.

When there is input from the end key of the ten-key pad 125, then in step S506 the controller 21 executes a process to end setting of the standard values and the routine returns to the process of step S4.

The process to end setting of the standard values includes a process for setting the changed upper limit values as the upper limit value of rank 1 and the upper limit value of rank 4 in the standard values table 71, and setting the lower limit value of rank 2 to a numeric value obtained by adding 0.1 to the upper limit value of rank 1, and setting the lower limit value of rank 5 to a numeric value obtained by adding 0.1 to the upper limit value of rank 4, and storing these values in the standard value storage area 27 of the memory 25.

The process for ending the setting of the standard values further includes a process for displaying a measurement screen for starting measurement on the display 9.

If there is no input from the end key of the ten-key pad 125 in step S505, the controller 21 again executes the process of step S504.

When it is determined in step S501 that the service F is not set at [1], the service setting process (step S8) ends, and the routine returns to the process of step S4.

Since the analyzer of the present embodiment does not display a parameter key on the display 9 unless operating under the service mode, a user cannot set the upper limit values of rank 1 and rank 4 unless the measurement device 1 is operating under the service mode. That is, when the measurement device 1 is operating under the user mode, the upper limit values of rank 1 and rank 4 are fixed values. However, the upper limit values of rank 2 and rank 3 are changeable numeric values the measurement device 1 is operating under either the user mode or service mode.

Since the analyzer of the present embodiment does not execute the standard value change reception process (step S504) insofar as the service F has not been set at [1], it is possible to reliably prevent changing the upper limit values of rank 1 and rank 4 when operating under the user mode.

Since the analyzer of the present embodiment separately displays a service standard value change screen 121 for changing the upper limit values of rank 1 and rank 4, an a user standard value change screen 75 for changing the upper limit values of rank 2 and rank 3, it is possible to prevent erroneously changing the upper limit values of rank 1 and rank 4 when changing the upper limit values of rank 2 and rank 3.

Figure 9:
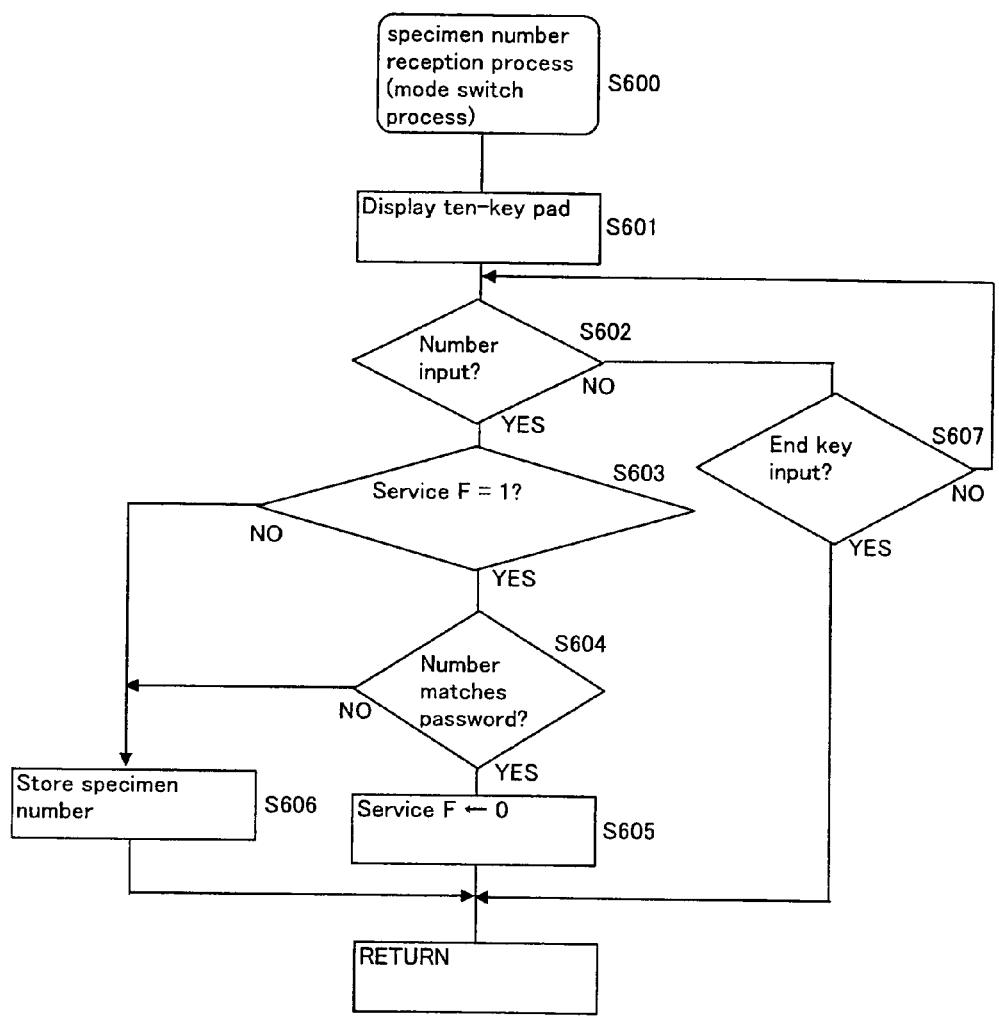
FIG. 9 is a flow chart showing details of the specimen number setting process (step S10)

Details of the specimen number setting process of step S10 are described below using FIG. 9.

In step S601, the controller 21 executes a process to display a ten-key pad identical in structure to the ten-key pad 90 shown in FIG. 11 on the display 9.

The controller 21 then executes a process to determine whether or not the specimen number (numbers and the like) is input by the ten-key pad displayed on the display 9, and whether or not there is input from the input key (step S602).

In step S603, the controller 21 determines whether or not the service F is set at [1]. When the service flag F is set at [1], the routine advances to the process of step S604, whereas when the service F is not set at [1], the routine advances to the process of step S606.

In step S604, the controller 21 executes a process to determine whether or not the input specimen number (numbers and the like) matches a predetermined password (second password) (step S604). The second password is different from the first password used in the mode switching process (step S2).

When the input specimen number (numbers and the like) matches the second password, the controller 21 sets the service F at [0] (step S605). In this way the analyzer body 1 operates under the user mode.

When the input specimen number (numbers and the like) does not match the second password, the controller 21 sets the input specimen number (numbers and the like) as the specimen number of the next urine (specimen) to be measured, and stores the number in the memory 25 (step S606).

When a specimen number (numbers and the like) is not input in step S602, the controller 21 executes a process to determine whether or not there has been input from the end key provided on the ten-key pad (step S607). Reception of a specimen number is ended when the user touches the end key.

When the end key is touched, the specimen number reception process (step S10) ends, and the routine returns to the process of step S4.

Figure 10:
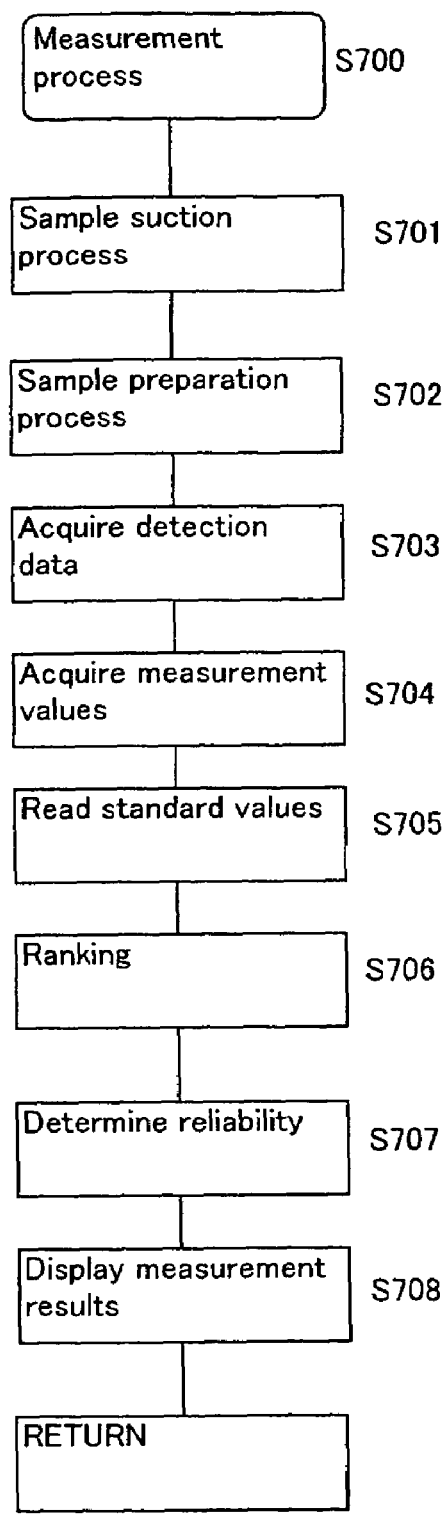
FIG. 10 is a flow chart showing details of the measurement process (step S12)

Details of the measurement process of step S12 are described below using FIG. 10.

In step S701, the controller 21 executes a process to suction urine from the specimen container by the suction unit 11.

Then, in step S702, the controller 21 executes a process to prepare a measurement sample by mixing urine and reagent using the sample preparation unit 13.

Next, in step S703, the controller 21 executes a process for detecting detection data from the measurement sample using the detection unit 15.

In step S704, the controller 21 executes a process to acquire measurement values from the detection data.

Specifically, the controller 21 creates scattergrams based on the scattered light information and fluorescent light information obtained by the detection unit 15. The numbers of red blood cells (RBC), white blood cells (WBC), epidermal cells (EC), columnar cells (CAST), and bacteria (BACT) are acquired (calculated) as measurement values based on the scattergrams and the voltage detected by the DC current circuit 29. The controller 21 also calculates the conductivity (COND) of the measurement sample as a measurement value based on the voltage of the measurement sample detected by the conductivity sensor 19.

In step S705, the controller 21 reads the standard values stored in the standard values storage area 27 of the memory 25.

In step S706, the controller 21 executes a process to rank (evaluate) the conductivity from rank 1 to rank 5 based on the conductivity and the standard values.

For example, when the standard values are set as shown in the standard values table 71 of FIG. 12, a conductivity of 0 or more but less than 5 is designated rank 1, conductivity of 5.1 or more but less than 16 is designated rank 2, conductivity of 16.1 or more but less than 27 is designated rank 3, conductivity of 27.1 or more but less than 38 is designated rank 4, and conductivity of 38.1 or more is designated rank 5.

In step S707, the controller 21 executes a process to determine whether or not the conductivity is a reliable value.

Specifically, the conductivity reliability is low when the conductivity is less than the upper limit value of rank 1, and more than the upper limit of rank 4. When the conductivity is such an unreliable value, the urine analyzer can be considered to have malfunctioned, or a fluid other than urine (for example, water) has been measured.

In step S708, the controller 21 displays the analysis result screen, which indicates the measurement value acquired in step S704, the ranking result acquired step S706, and the reliability determined in step S707, on the display 9.

Figure 15:
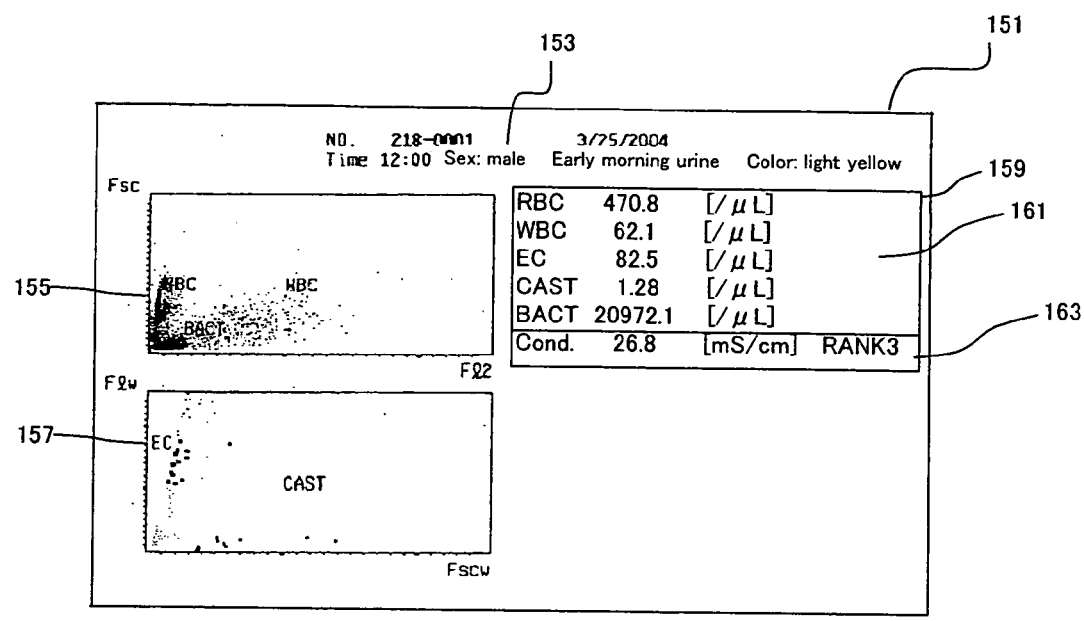
FIG. 15 shows an analysis result screen 151.

FIG. 15 shows the analysis result screen 151 displayed on the display 9.

The analysis result screen 151 includes an attribute display area 153 which shows urine attributes, scattergram display areas 155 and 157 which show the scattergrams created based on the scattered light information and fluorescent light information, and an analysis result display area showing the urine analysis results including the measurement values.

The attribute display area 153 includes information such as the specimen number, time the specimen was measured, sex of the subject, urine type, and urine color and the like. The number set in the specimen number setting process (step S10) is displayed as the specimen number.

The analysis result display area 159 includes a five item display area 161 for displaying the numbers of red blood cells (RBC), white blood cells (WBC), epidermal cells (EC), columnar cells (CAST), bacteria (BACT), and a conductivity display area 163 for displaying the conductivity (COND).

The conductivity display area 163 displays the conductivity calculated in step S704 (26.8 in FIG. 15), the units of conductivity displayed in the adjacent right side of the conductivity (mS/cm in FIG. 15), and the rank determined in step S706 appears to the adjacent right of the units (rank 3 in FIG. 15). When rank 1 or rank 5 appear in the conductivity, an asterisk mark [*] indicating low reliability is displayed between the conductivity and the units.

Since the upper limit value of rank 1 and the upper limit value of rank 4 are fixed values and the upper limit value of rank 2 and the upper limit value of rank 3 are changeable values in the previously described embodiment, the standard values which should not be optionally changeable of the upper limit value of rank 1 and the upper limit value of rank 4 are not changeable, and the standard values which should be optionally changeable of the upper limit value of rank 2 and the upper limit value of rank 3 are changeable.

In this way the urine analyzer of the present embodiment prevents a user from inappropriately changing standard values which should not be changed.

For example, if the users of the urine analyzer are not taught the method for switching to the service mode, and only the person responsible for the maintenance of the urine analyzer is learns the method for switching to the service mode, then the users cannot change the standard values which should not be optionally changeable of the upper limit value of rank 1 and the upper limit value of rank 4, and can change the standard values which should be optionally changeable of the upper limit value of rank 2 and the upper limit value of rank 3.

When is necessary to change the upper limit value of rank 1 and the upper limit value of rank 4, the person responsible for maintenance of the urine analyzer can change those standard values.

The above described embodiment should not be considered as limited in any respect to the examples given. The scope of the present invention is described by the scope of the claims and not by the description of the above embodiment, and further includes all modifications within the scope of the claims and all equivalences of meaning within the scope of the claims.

Although the present embodiment as been described in terms of a urine analyzer which switches to the service mode when a predetermined password is entered after a specific position on the display 9 has been touched within a predetermined time after the power has been turned ON, the present invention is not limited to this example inasmuch as the present invention is also applicable to urine analyzers which operate only in a user mode and cannot switch to a service mode.

Furthermore, the present invention is also applicable to urine analyzers which automatically switch to a service mode when a specific position on the display 9 is touched within a predetermined time after the power has been turned ON.

Furthermore, although password entry is required to switch from the service mode to the user mode in the previously described embodiment, the present invention is not limit to this arrangement inasmuch as the mode may also be automatically switched to the user mode when a predetermined button is touched.

Although the upper limit value of rank 1 and the upper limit value of rank 4 are fixed values in the user mode and these standard values are changeable values in the service mode in the above described embodiment, the present invention is not limited to this arrangement inasmuch as these standard values also may be fixed values in the service mode.

Although the upper limit value of rank 1 and the upper limit value of rank 4 are changeable values in the service mode and these standard values in the above described embodiment, the present invention is not limited to this arrangement inasmuch as only one value among either the upper limit value of rank 1 or the upper limit value of rank 4 may be a changeable value.

Although the upper limit value of rank 1 and the upper limit value of rank 4 are fixed values in the user mode and the upper limit value of rank 2 and the upper limit value of rank 3 are changeable values in the user mode in the above described embodiment, the present invention is not limited to this arrangement inasmuch as these the upper limit value of rank 1 and the upper limit value of rank 4 may be changeable values and the upper limit value of rank 2 and the upper limit value of rank 3 may be fixed values in the user mode.

Although the upper limit value of rank 2 and the upper limit value of rank 3 are changeable values in the user mode and the service mode in the above described embodiment, the present invention is not limited to this arrangement inasmuch as these standard values may be changeable in the user mode and also be fixed values in the service mode. In this way erroneous changing of the upper limit value of rank 2 and upper limit value of rank 3 in the service mode can be prevented. Changing of standard values in the service mode is easily accomplished since all standard values are changeable in the service mode if the upper limit value of rank 2 and the upper limit value of rank 3 are changeable in both the user mode and the service mode as in the above described embodiment.

In the above embodiment, a user standard value change screen 75 is displayed on the display 9 as a screen for changing the upper limit value of rank 2 and the upper limit value of rank 3, and a service standard value change screen 121 is displayed on the display 9 as a screen for changing the upper limit value of rank 1 and the upper limit value of rank 4, however, the present invention is not limited to this arrangement inasmuch as these standard values also may be changed from the same screen.

Although the above embodiment is configured such that the lower limit value of the next higher rank is automatically changed when the upper limit value of a rank is changed, the present invention is not limited to this arrangement inasmuch as the upper limit value of the next lower rank also may be automatically changed when a lower limit value of a rank is changed. Furthermore, both upper limit values and lower limit values may also be optionally changeable.

Although the memory 25 stores only one set of standard values in the above embodiment, the present invention is not limited to this arrangement inasmuch as a plurality of standard values may also be stored in accordance with attributes such as subject (patient) sex, age, and state of disease and the like. For example, standard values for female patients and standard values for male patients may be respectively stored in the memory 25. In this case, the controller 21 may automatically select the female or male standard values in accordance with the sex of the patient, and use the selected standard values for the conductivity ranking.

Although the conductivity evaluation result is displayed in text from rank 1 to rank 5, in the above embodiment the present invention is not limited to this arrangement inasmuch as the result may also be displayed in text as large, intermediate, and small, or the magnitude of the conductivity may be represented by a number of [+] symbols, or a line representing the evaluation result may be provided such that the magnitude of the conductivity is represented by the length of the line.

Although both the conductivity and ranking are displayed on the measurement result screen 151 in the above embodiment, the present invention is not limited to this arrangement inasmuch as the ranking alone may be displayed without displaying the conductivity.

Although only conductivity is ranked in the above embodiment, the numbers of red blood cells (RBC), white blood cells (WBC), epidermal cells (EC), columnar cells (CAST), and bacteria (BACT) also may be ranked.

Although the above embodiment describes a urine analyzer for analyzing tangible material in urine as an example of the analyzer of the present invention, the present invention is not limited to this example inasmuch as the present invention is also applicable to urine qualitative analyzers which immerse a test sheet to which reaction test papers for separate measurement items have been adhered into a urine sample for a predetermined time, compare the test sheet colors with determination standard colors, and automatically acquire the degree of color change for each measurement item as a measurement value. In this case, the degree of color change can be classified as [−], [±], [+], [2+], and [3+], and changeable values and fixed values may also be provided as standard values for classifying these degrees of color change.

Although the above embodiment describes a urine analyzer for analyzing tangible material in urine as an example of the analyzer of the present invention, the present invention is not limited to this example inasmuch as the present invention is also applicable to analyzers other than urine analyzers, such as blood analyzers and the like.

Although the above embodiment describes a urine analyzer for analyzing tangible material in urine as an example of the analyzer of the present invention, the present invention is not limited to this example inasmuch as the present invention is also applicable to programs stored in the ROM of memory 25 of the previously described urine analyzer. The present invention is further applicable to computer-readable recording media (for example, CD-ROM and DVD-ROM) for recording the aforesaid programs.

What is claimed is:

1. An analyzer comprising:
   a sample measuring section for measuring a sample and generating a measurement value;
   a memory for storing a plurality of standard values for evaluation of the measurement value, the plurality of standard values including a fixed standard value and a variable standard value;
   an evaluation means for evaluating the measurement value based on the standard values;
   an output device for outputting result of the evaluation of the measurement value by the evaluation means; and
   a standard value changing means for displaying the variable standard value stored in the memory on the output device, and changing the displayed variable standard value;
   wherein the standard value changing means displays a variable standard value change screen which includes the variable standard value and the fixed standard value on the output device, and changes the variable standard value displayed on the variable standard value change screen.

2. An analyzer comprising:
   a sample measuring section for measuring a sample and generating a measurement value;

a memory for storing a plurality of standard values for evaluation of the measurement value, the plurality of standard values including a fixed standard value and a variable standard value;

an evaluation means for evaluating the measurement value based on the standard values;

an output device for outputting result of the evaluation of the measurement value by the evaluation means;

a standard value changing means for displaying the variable standard value stored in the memory on the output device, and changing the displayed variable standard value; and a service mode setting means for setting the analyzer to operate in a service mode;

wherein the fixed standard value can be changed by the standard value changing means when the analyzer is set to operate in the service mode.

3. The analyzer of claim 2 wherein the service mode setting means includes a password receiving means for receiving a password; and a setting control means for setting the analyzer to operate in the service mode when the password received by the password receiving means is correct.

4. The analyzer of claim 2, wherein, when the analyzer is set to operate in the service mode, the standard value changing means displays a fixed standard value change screen which includes fixed standard value, and changes the fixed standard value displayed on the fixed standard value change screen.

5. The analyzer of claim 1, wherein the evaluation means ranks the measurement value based on the magnitude of the measurement value and the standard values; and the fixed standard value is a standard value which divides a rank representing a minimum domain of a measurement value from a rank representing a second smallest domain of a measurement value.

6. The analyzer of claim 1, wherein the evaluation means ranks the measurement value based on the magnitude of the measurement value and the standard values; and the fixed standard value is a standard value which divides a rank representing a maximum domain of a measurement value from a rank representing a second largest domain of a measurement value.

7. An analyzer comprising:

a sample measuring section for measuring a sample and generating a measurement value;

a memory for storing a plurality of standard values for evaluation of the measurement value, the plurality of standard values including a fixed standard value and a variable standard value;

an evaluation means for evaluating the measurement value based on the standard values;

an output device for outputting result of the evaluation of the measurement value by the evaluation means; and a standard value changing means for displaying the variable standard value stored in the memory on the output device, and changing the displayed variable standard value;

wherein the output device outputs a result screen which includes the measurement value and the evaluation result.

8. The analyzer of claim 1 further comprising a determination means for determining whether or not the measurement value is reliable based on the measurement value and the fixed standard value.

9. The analyzer of claim 1, wherein the sample measuring section includes a sample preparation section for preparing a measurement sample by mixing the sample and reagent, a detection section for detecting electrical information from the measurement sample, and a conductivity calculation means for calculating conductivity of the sample from the electrical information;

wherein the measurement value includes the conductivity.

10. A computer program product comprising:

a computer readable medium; and computer instructions, on the computer readable medium, for enabling a computer to perform the operations of:

measuring a sample and generating a measurement value;

storing a plurality of standard values for evaluation of the measurement value, the plurality of standard values including a fixed standard value and a variable standard value;

evaluating the measurement value based on the standard values; and outputting result of the evaluation of the measurement value; and displaying the variable standard value stored in a memory on an output device,and changing the displayed variable standard value;

wherein the output device outputs a result screen which includes the mearsurement value and the evaluation result.

11. An analyzer comprising:

a sample measuring section for measuring a sample and generating a measurement value;

a display device; a memory for storing first and second standard values for evaluating the measurement value;

a first standard value setting means for displaying a first screen including the first standard value on the display device, and receiving a change of the first standard value; and a second standard value setting means for displaying a second screen including the second standard value on the display device, and receiving a change of the second standard value wherein the analyzer operates in a first mode in which the first standard value cannot be changed by the first standard value setting means, and a second mode in which the first standard value can be changed by the first standard value setting means.

12. The analyzer of claim 11 further comprising a mode switching means for switching a mode of the analyzer from a first mode to a second mode; wherein the mode switching means includes a password receiving means for receiving a password, and a switch permission means for permitting the mode to be switched based on the received password.

13. The analyzer of claim 12 further comprising a second mode switching means for switching a mode of the analyzer from the second mode to the first mode.

14. The analyzer of claim 11, wherein changing the second standard value by the second standard value setting means is possible in the first mode and the second mode.

15. The analyzer of claim 11, wherein the first screen cannot be displayed by the display device in the first mode, and the first screen can be displayed by the display device in the second mode.

16. The analyzer of claim 15 further comprising a key display means which does not display a key for displaying the first screen on the display device in the first mode, and does display the key on the display device in the second mode.

17. The analyzer of claim 11, wherein the second screen further includes the first standard value.

18. An analyzer comprising:
a sample measuring section for measuring a sample and generating a measurement value;
a display device;
a memory for storing first and second standard values for evaluating the measurement value;
a first standard value setting means for:
displaying a first screen including the first standard value on the display device, and
receiving a change of the first standard value; and
a second standard value setting means for:
displaying a second screen including the second standard value on the display device, and
receiving a change of the second standard value;
wherein the second screen further includes the first standard value.

19. The analyzer of claim 2, further comprising determination means for determining whether the measurement value is reliable based on the measurement value and the fixed standard value.

20. The analyzer of claim 7, further comprising determination means for determining whether the measurement value is reliable based on the measurement value and the fixed standard value.

* * * * *